(12) United States Patent
Sholev

(10) Patent No.: US 8,690,755 B2
(45) Date of Patent: *Apr. 8, 2014

(54) ENDOSCOPIC POSITIONING SYSTEM

(75) Inventor: Mordehai Sholev, Amikam (IL)

(73) Assignee: M. S. T. Medical Surgery Technologies Ltd., Yoqneam (IL)

( * ) Notice: Subject to any disclaimer, the term of this patent is extended or adjusted under 35 U.S.C. 154(b) by 996 days.

This patent is subject to a terminal disclaimer.

(21) Appl. No.: 12/441,838

(22) PCT Filed: Sep. 20, 2007

(86) PCT No.: PCT/IL2007/001161
§ 371 (c)(1),
(2), (4) Date: Mar. 18, 2009

(87) PCT Pub. No.: WO2008/035345
PCT Pub. Date: Mar. 27, 2008

(65) Prior Publication Data
US 2009/0312600 A1    Dec. 17, 2009

Related U.S. Application Data

(60) Provisional application No. 60/846,109, filed on Sep. 21, 2006.

(51) Int. Cl.
*A61B 1/00* (2006.01)
*A61B 1/04* (2006.01)

(52) U.S. Cl.
USPC ............................ 600/102; 600/114; 600/117

(58) Field of Classification Search
USPC .......................................... 600/117, 102, 114
See application file for complete search history.

(56) References Cited

U.S. PATENT DOCUMENTS

| 4,559,928 | A | * | 12/1985 | Takayama | 600/152 |
|---|---|---|---|---|---|
| 5,154,723 | A | * | 10/1992 | Kubota et al. | 606/130 |
| 5,201,742 | A | | 4/1993 | Hasson | |
| 5,571,072 | A | | 11/1996 | Kronner | |
| 5,878,193 | A | | 3/1999 | Wang et al. | |
| 6,024,695 | A | * | 2/2000 | Taylor et al. | 600/102 |
| 6,997,866 | B2 | | 2/2006 | Payandeh et al. | |
| 7,048,745 | B2 | | 5/2006 | Tierney et al. | |
| 2003/0233102 | A1 | * | 12/2003 | Nakamura et al. | 606/130 |
| 2011/0257475 | A1 | * | 10/2011 | Berkelman et al. | 600/102 |

FOREIGN PATENT DOCUMENTS

WO    2006111966  A2    10/2006

OTHER PUBLICATIONS

International Search Report mailed Sep. 12, 2008 for PCT/IL2007/001161 filed Sep. 20, 2007.
Written Opinion mailed Sep. 12, 2008 for PCT/IL2007/001161 filed Sep. 20, 2007.
International Preliminary Report on Patentability published Apr. 4, 2009 for PCT/IL2007/001161 filed Sep. 20, 2007.

* cited by examiner

*Primary Examiner* — Philip R Smith
*Assistant Examiner* — Rynae Boler
(74) *Attorney, Agent, or Firm* — The Law Office of Michael E. Kondoudis

(57) ABSTRACT

The present invention discloses an endoscope positioning system for maneuvering, orienting and positioning an endoscope relative to an organ within a patient's body during an endoscopic operation. The endoscope positioning system comprises a gripper that reversibly attaches the positioning system to the patient's body while allowing full adjustment of the endoscope in four degrees of freedom.

21 Claims, 19 Drawing Sheets

US 8,690,755 B2

ENDOSCOPIC POSITIONING SYSTEM

FIELD OF THE INVENTION

This invention relates to a structure for supporting a surgical instrument, such as an endoscope, and more particularly to a structure which provides for repositioning of the instrument during surgery without stressing an incision through which the instrument extends.

BACKGROUND OF THE INVENTION

Laparoscopic surgery is a procedure in which surgical instruments and a viewing scope, referred to generally as an endoscope and more specifically as a laparoscope, are inserted through small puncture wounds or incisions into the abdominal cavity of a patient. A small video camera is attached to the laparoscope and connected to a television monitor for viewing the procedure.

The instruments and the laparoscope are inserted through cannulae which are first inserted through the incisions. Cannulae are hollow tubes with gas valves. The cannulae are left in the puncture wounds throughout the procedure. This allows the instruments and scope to be removed and reinserted as necessary.

To aid in visualizing the intra-abdominal structures, gas is inserted through one of the cannulae to raise the abdominal wall. Seals are required at the exit points of the scope and instruments to prevent the gas from escaping.

The viewing laparoscope is inserted through a cannula which is usually inserted through an incision made in the umbilicus. The scope is then directed toward the pelvis for pelvic surgery or toward the liver for gallbladder surgery.

Throughout the procedure it is necessary for the surgeon, assistant surgeon, or a scrub nurse to hold the scope and direct it at the target of the surgery. It is constantly being repositioned to obtain the best view. This process ties up one hand of the surgeon or assistant surgeon, if either holds the scope. The scrub nurses also have other tasks to perform, and holding the scope interferes with performing these tasks. It is also difficult for the surgeon to direct others to position the scope for the best view. When the scope is not held by the surgeon, it is often misdirected.

The support of a laparoscope has been provided through the use of robotic retractors. Retractors hold instruments in fixed positions, such as for holding an incision open to allow a surgeon access to the underlying body parts. The retractors are fixedly clamped to a mechanical skeleton. This skeleton has also been used to hold a laparoscope in a fixed position. When it is desired to move the scope, the clamp must be readjusted, and usually the skeleton linkages must also be adjusted to accommodate a change in the angle of insertion of the laparoscope.

U.S. Pat. No. 5,571,072 ('072) discloses a cannula and an associated endoscope secured to an operating table by a mechanical linkage assembly having linear and angular connections. These connections are adjustable for supporting an endoscope extending through an incision. According to '072, two angular connections are friction joints that allow manual repositioning of the scope by pivoting about respective orthogonal axes that intersect at a point along the scope that is coincident with the location of the incision.

U.S. Pat. No. 7,048,745 ('745) teaches surgical tool robotic manipulator. As taught by '745 embedded computer means can perform a number of functions when the tool is loaded on the tool manipulator: (1) providing a signal verifying that the tool is compatible with that particular robotic system; (2) identifying the tool-type to the robotic system so that the robotic system can reconfigure the programming; or (3) indicating tool-specific information, including measured calibration offsets indicating misalignment of the tool drive system, tool life data, or the like.

Patent Application WO2006111966 ('966) to the inventor, which is incorporated as a reference, discloses a computerized system enabling operative precise positioning laparoscopic surgical tools. The system comprises a manipulator providing displacement in four degree of freedom. The system consists of two main components: the first part has an arc shape in which the endoscope can be driven back and forth and at the same time can be moved from side to side; the second part is characterized by zoom and rotation properties.

Laparoscopic orthopedic surgeries differ from abdominal laparoscopic surgeries in their dynamic nature: it is common in orthopedic surgeries to move the limbs of the patient from side to side to bend the knee or the shoulder, or to stretch the patient's joints. Traditional endoscope holders are fixed to the operation table and do not let the endoscope follow the limb movement and therefore are not used in these kinds of procedures. Today, endoscopic orthopedic procedures are performed by the surgeon holding the endoscope in one hand and using a tool in the other hand. When the surgeon needs to use two tools at the same time, he requires an assistant to hold and aim the endoscope for hint. Hence, a system providing rigid fixation of the laparoscope relative to the human limb and laparoscope precise moving, especially a system with four or more degrees of freedom is still a long-felt need.

SUMMARY OF THE INVENTION

It is one object of the present invention to provide an endoscope positioning system (EPS, 300) for maneuvering, orienting and positioning an endoscope 500 relatively to an organ being operated within a patient's body; said EPS is especially used during orthopedic operations such that said organ is constantly moved during said operation;
said EPS comprising:
 a. at least four freedom degree mechanisms (FDFM) (100); said FDOF are adapted to actuate the distal portion of said endoscope by maneuvering the proximal portion of said endoscope; said FDFM comprises at least a first, second, third and fourth means for providing said four degrees of freedom:
  i. said means of first degree of freedom is a rotation gab-mechanism 310 adapted to rotate said endoscope around its longitudinal axis;
  ii. said means of second degree of freedom is a tilting sub-mechanism 320, comprising:
   a. at least one transmission 116 in mechanical communication with arc 150; said arc 150 is in mechanical communication with said endoscope; and,
   b. at least one motor 157b in reversible mechanical communication with said transmission 116; said transmission 116 is adapted to transmit rotational motion from said motor 157b to said arc 150 such that said arc 150 is titled at an angle of interest;
  iii. said means of third degree of freedom is an arc sub-mechanism 330, comprising:
   a. at least one nut 151 adapted to linearly move along at least one screw (155);
   b. a chain comprising a plurality of links, said chain is characterized by having a distal end and a proximal end; each of said links is in mechanical communication with at least one of its neighboring links; said chain is at least partially located in semicircular guides (154);

said at least one nut 151 is in mechanical communication with at least one first link (152a) in said proximal end of said chain;

a gimbal (170) through which said endoscope passes is in mechanical communication with at least one link located in said distal end of said chain;

wherein said linear movement of said nut (151) is adapted to affects said first link (152a) in said chain such that the remaining links in said chain are forced to move along said semicircular guides 154 so as to move said gimbal 170 and said endoscope 500 along said arc 150;

iv. said means of fourth degree of freedom is a zoom sub-mechanism 340;

each of said first, second, third and fourth degree of freedom is characterized by an independent movement;

b. at least one body adapter gripper (201) adapted to reversibly and firmly attach said EPS to said patient's body;

wherein said EPS is conformed to said movements of said organ by means of said gripper 201 such that the orientation of said endoscope is adjustable accordingly to said movement.

It is another object of the present invention to provide the EPS as defined above, wherein said EPS is adapted to maintain a constant orientation of said endoscope relatively to said organ by means of said gripper 201, such that alteration in said orientation as a result of said movements of said organ is prevented.

It is another object of the present invention to provide the EPS as defined above, wherein at least one of said first, second, third and fourth means for providing degrees of freedom is activated by a mechanical or electrical motoring means.

It is another object of the present invention to provide the EPS as defined above, wherein said gripper are selected from a group consisting of strips, magnets, screws, hooks, zips, fasteners, clips, flaps, claspers, springs, grips, hooks-and-loops (especially Velcro™-type fasteners), hooks, hooks and eyes, straps, strings, wires, cables, tabs, links, poppers, nails, buttons, brackets, buckles or any combination thereof.

It is another object of the present invention to provide the EPS as defined above, wherein said motoring means activates at least one of said first, second, third and fourth means for providing degrees of freedom by maneuvering said first, second, third and fourth means relative to said gripper 201.

It is another object of the present invention to provide the EPS as defined above, wherein said motoring means comprises a plurality of motors, at least two motors are adapted to simultaneously actuate said at least a first, second, third and fourth means for providing degrees of freedom.

It is another object of the present invention to provide the EPS as defined above, wherein said motoring means and said at least a first, second, third and fourth means for providing degrees of freedom are reversibly interconnected.

It is another object of the present invention to provide the EPS as defined above, wherein said tilting sub-mechanism 320 is characterized in that the reciprocal movement of gimbal 170 along arc 150, and tilting of arc 150 are completely independent movements.

It is another object of the present invention to provide the EPS as defined above, wherein said zoom sub-mechanism 340 comprises:

a. at least one worm gear 181;

b, at least one drum 182 mechanically connected to said worm gear 181; said drum 182 is characterized by a main longitudinal axis; said drum 182 is adapted to rotate a wire 183 around said main axis, such that the distance between said drum 183 and a gimbal 170 is shortened and a zoom motion is obtained.

It is another object of the present invention to provide the EPS as defined above, additionally comprising a quick locking sub-mechanism 350, adapted to enable or disenable said arc sub-mechanism 330.

It is another object of the present invention to provide the EPS as defined above, additionally comprising a quick fixing sub-mechanism 370 adapted to reversibly connect said endoscope 500 from semicircular guides (154); said quick fixing sub-mechanism 370 comprising:

a. gimbal 170 through which said endoscopes passes;

b. at least one screw 161;

c. a cylinder 162 adapted to partially and reversibly accommodate said screw 161;

d. at least one clamping means 163 reversibly housed within said cylinder 162; said clamping means 163 being in mechanical communication with said screw 161; said clamping means 163 are adapted to reversibly apply pressure on said cylinder such that said gimbal 170 is reversibly housed within said cylinder 162.

It is another object of the present invention to provide a method for maneuvering, orienting and positioning an endoscope 500 relative to an organ being operated within a patient's body, during orthopedic operations such that said organ is constantly moved during said operation. The method comprises steps selected inter alia from:

a. obtaining an endoscope positioning system (EPS, 300); said EPS comprising:

i. at least four freedom degree mechanisms (FDFM) (100) comprising at least a first, second, third and fourth means for providing said four degrees of freedom:

a. said means of first degree of freedom is a rotation sub-mechanism 310 adapted to rotate said endoscope around its longitudinal axis;

b. said means of second degree of freedom is a tilting sub-mechanism 320, comprising:

i. at least one transmission 116 in mechanical communication with arc 150; said arc 150 is in mechanical communication with said endoscope; and, ii. at least one motor 157b in reversible mechanical communication with said transmission 116;

said transmission 116 is adapted to transmit rotational motion from said motor 157b to said arc 150 such that said arc 150 is titled at an angle of interest;

c. said means of third degree of freedom is an arc sub mechanism 330, comprising:

i. at least one nut 151 adapted to linearly move along at least one screw (155);

ii. a chain comprising a plurality of links, said chain is characterized by having a distal end and a proximal end; each of said links is in mechanical communication with at least one of its neighboring links; said chain is at least partially located in semicircular guides (154);

said at least one nut 151 is in mechanical communication with at least one first link (152*a*) in said proximal end of said chain;

a gimbal (170) through which said endoscope passes is in mechanical communication with at least one link located in said distal end of said chain;

wherein said linear movement of said nut (151) is adapted to affects said first link (1.52*a*) in said chain such that the remaining links in said chain are forced to move along said semicircular guides 154 so as to move said gimbal 170 and said endoscope 500 along said arc 150;

d. said means of fourth degree of freedom is a zoom sub-mechanism 340;

each of said first, second, third and fourth degree of freedom is characterized by an independent movement;

ii. at least one body adapter gripper (201);

b. reversibly and firmly attaching said EPS to said patient's body via said body adapter gripper (201);

c. maneuvering the proximal portion of said endoscope in a movement selected from a group consisting of rotating, tilting, arcing or zooming thereby actuating and orienting the distal portion of said endoscope;

wherein said step of reversibly and firmly attaching said EPS to said patient's body conforms said EPS is to said movements of said organ by means of said gripper 201 such that the orientation of said endoscope is adjustable accordingly to said movement.

It is another object of the present invention to provide the method as defined above, wherein said step of reversibly and firmly attaching said EPS to said patient's body maintains said endoscope of said EPS in a constant orientation relatively to said organ by means of said gripper 201, such that alteration in said orientation as a result of said movements of said organ is prevented.

It is still an object of the present invention to provide the method as defined above, wherein said step of actuating and orienting the distal portion of said endoscope is performed by mechanical or electrical motoring means 110.

It is lastly an object of the present invention to provide the method as defined above, additionally comprising step of selecting said gripper from a group consisting of strips, magnets, screws, hooks, zips, fasteners, clips, flaps, claspers, springs, grips, hooks-and-loops (especially Velcro™ m-type fasteners), hooks, hooks and eyes, straps, strings, wires, cables, tabs, links, poppers, nails, buttons, brackets, buckles or any combination thereof.

BRIEF DESCRIPTION OF THE FIGURES

The objects and advantages of various embodiments of the invention will become apparent from the following description when read in conjunction with the accompanying drawings, wherein.

DETAILED DESCRIPTION OF THE EMBODIMENTS

Figure 1:
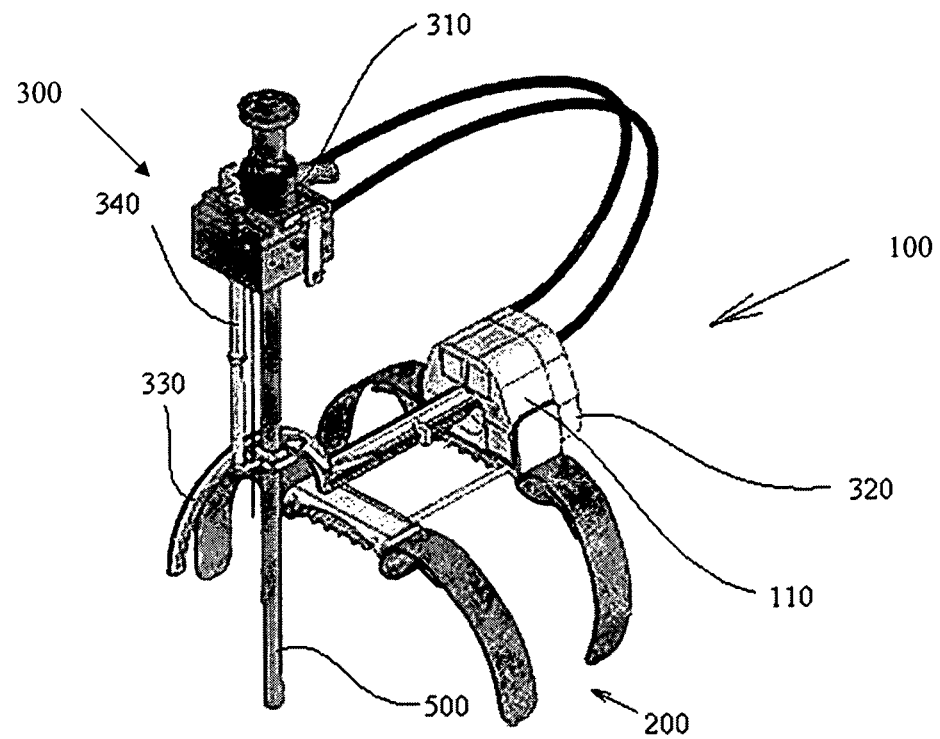
FIG. 1 is an isometric view of a four degree mechanism with an adapter.

The following description is provided in order to enable any person skilled in the art to make use of said invention and sets forth the best modes contemplated by the inventor of carrying out this invention. Various modifications, however, will remain apparent to those skilled in the art, since the generic principles of the present invention have been defined specifically to provide (i) an endoscope positioning system (EPS) essentially consisting at least four freedom degree mechanism (FDFM); (ii) a method of manipulating an endoscope in at least four degrees of freedom by the EPS; and (iii) method for applying endoscopic surgery.

The terms "endoscope" and "laparoscope" refer interchangeably hereinafter to a fiber optical device that consists of a flexible tube. Glass or plastic filaments allow the internal refraction of light for viewing. This medical device is used in laparoscope, endoscope, laparoscopic and endoscopic surgeries. It is also in the scope of the invention wherein the term refers also to any means for looking within body cavities, especially inside the human body and mammalian body for medical reasons using an instrument; and especially to means for minimally invasive diagnostic medical procedure, such as rigid or flexible endoscopes, fiberscopes, means for robotic surgery, trocars, surgical working tools and diagnosing means etc.

The terms "endoscopic surgery" and "laparoscopic surgery" interchangeably refer hereinafter to modern surgical technique in which operations into the body of a patient, e.g., in the abdomen, are performed through small incisions (usually 0.5 to 1.5 cm) as compared to larger incisions needed in traditional surgical procedures, or via natural cavities of the body. Laparoscopic surgery includes e.g., operations within the abdominal, pelvic or joint cavities. Endoscopy surgery involves, inter alia, operations in the gastrointestinal tract, e.g., in the oesophagus, stomach and duodenum (esophagogastroduodenoscopy), small intestine, colon (colonoscopy, proctosigmoidoscopy), bile duct, endoscopic retrograde cholangiopancreatography (ERCP), duodenoscope-assisted cholangiopancreatoscopy, intraoperative cholangioscopy, the respiratory tract, the nose (rhinoscopy), the lower respiratory tract (bronchoscopy), the urinary tract (cystoscopy), the female reproductive system, the cervix (colposcopy), the uterus (hysteroscopy), the Fallopian tubes (falloscopy), normally closed body cavities (through a small incision), the abdominal or pelvic cavity (laparoscopy), the interior of a joint (arthroscopy) organs of the chest (thoracoscopy and mediastinoscopy), during pregnancy, the amnion (amnioscopy), the fetus (fetoscopy), plastic surgery, panendoscopy (or triple endoscopy), combining laryngoscopy, esophagoscopy, and, bronchoscopy; and various non-medical uses for endoscopy. It is also in the scope of the invention wherein the term also refers also to any manipulation of laparoscopes and endoscopes as defined above into the body of a patient.

The invention concerns an endoscope positioning system suited for all kinds of laparoscopic surgeries. It is best suited for orthopedic surgeries as defined below. Laparoscopic orthopedic surgeries differ from abdominal laparoscopic surgeries in their dynamic nature: it is common in orthopedic surgeries to move the limbs of the patient from side to side; to bend the knee or the shoulder; or to stretch the patient's joints. Traditional endoscope holders are fixed to the operation table and therefore do not allow the endoscope to follow the limb movement and thus are not used in these kinds of procedures.

Today, endoscopic orthopedic procedures are performed by the surgeon holding the endoscope in one hand and using a tool in the other hand. When the surgeon needs to use two tools at the same time, he requires an assistant to hold and aim the endoscope for him.

The present invention provides a quick and optimal endoscope setup, automatic and precise positioning of the endoscope, which allows the surgeon to use both his arms for simultaneously operating two tools at the same time, without interfering with the flow of the operation process.

The term "Degrees of freedom" (DOE) refers hereinafter to a set of independent displacements that specify completely the displaced position of the endoscope or laparoscope as defined above. In three dimensional space, there are six DOE, three DOE of linear displacement and three rotational DOB, namely, moving up and down, moving left and right, moving forward and backward, tilting up and down, turning left and right, tilting side to side. The present invention refers to a system essentially comprising means for at least four DOE selected from any of those defined above.

The terms "distal portion" and "proximal portion" refer hereinafter to the side of the endoscope within the body of the patient, and outside the body of the patient, respectively.

Reference is now made to FIG. 1, illustrating a typical endoscope positioning system 300 comprising a four freedom degree mechanism (FDFM) that moves the endoscope 500 and the body adapter 200, thus enabling an optimal placement of the mechanism. The mechanism 100 comprises a rotation sub-mechanism 310, a tilting sub-mechanism 320, an arc sub-mechanism 330, and a zoom sub-mechanism 340. The sub-mechanisms 310, 320, 330, and 340 are activated by a motor box 110.

Figure 2:
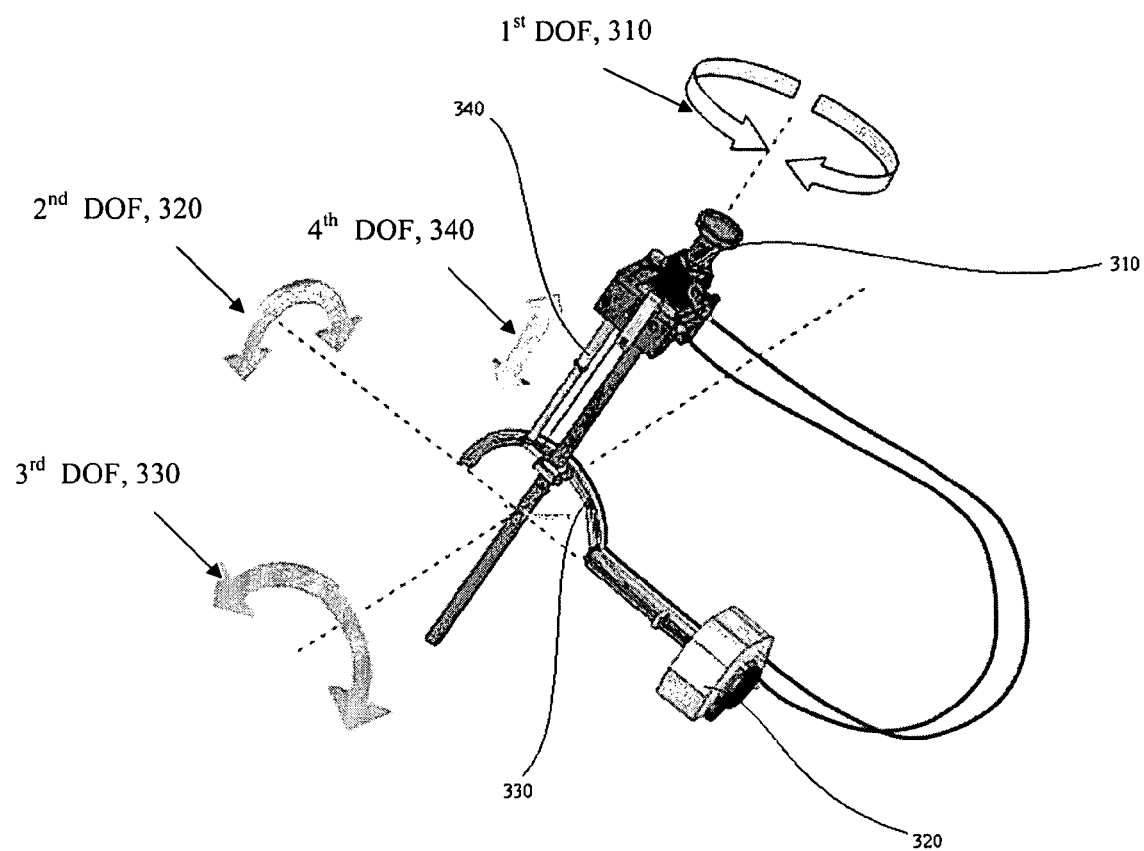
FIG. 2 is a schematic view representing four degree displacement.

Reference is now made to FIG. 2 showing the mechanism 300 enabling displacement of the endoscope 500 with FDFM. FDFM 300 is used for linearly and angularly positioning the endoscope 500 relative to a joint incision.

Figure 3A:
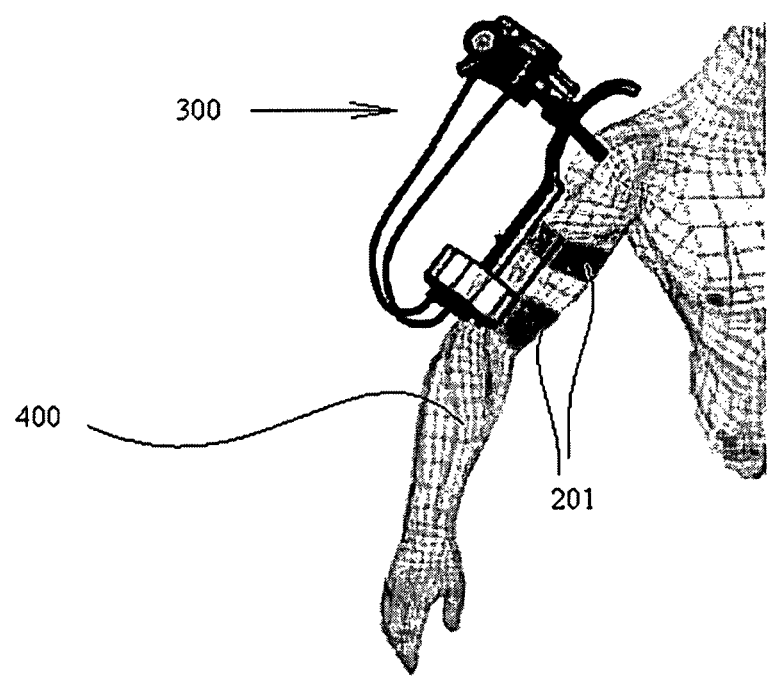
FIGS. 3*a*-3*c* are schematic views showing optional working arrangements for shoulder (3*a*) and knee (3*b* and 3*c*) surgery.
Figure 3B:
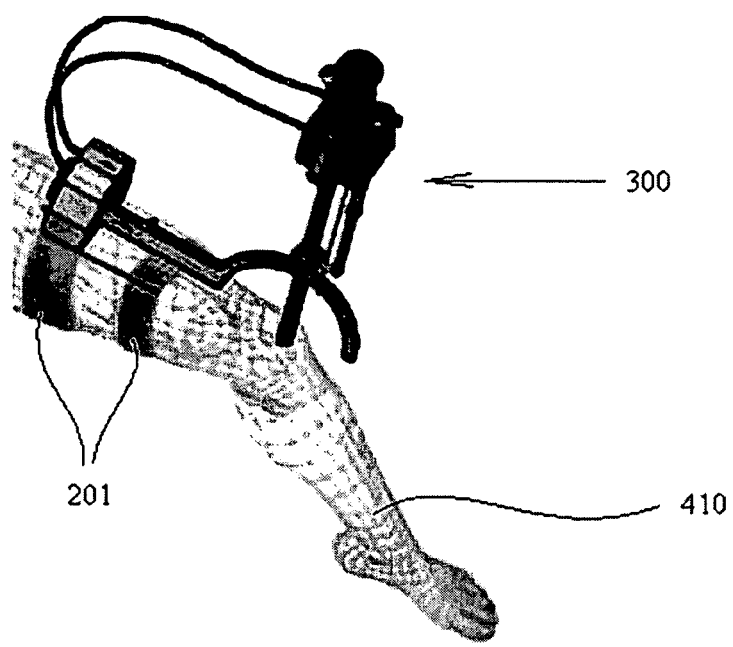
Figure 3C:
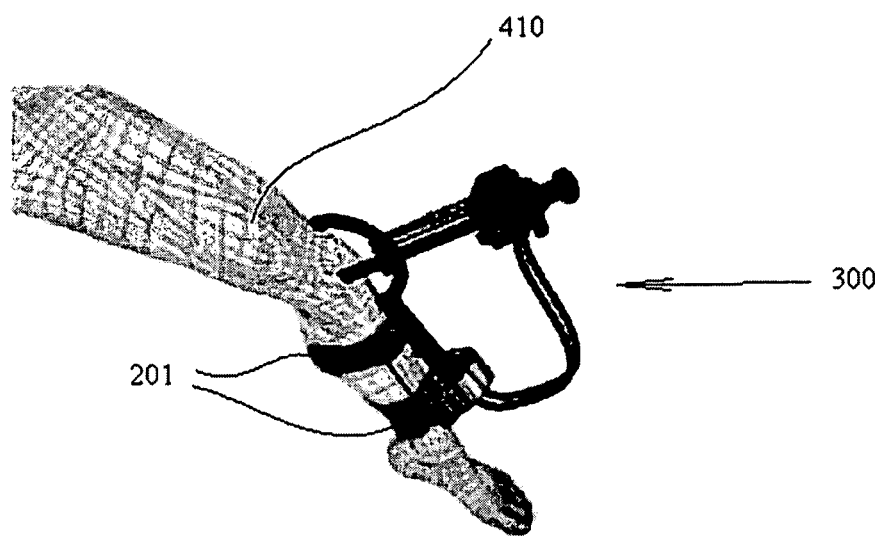

Reference is now made to FIG. 3, illustrating optional arrangements of the endoscope positioning system 300 on human limbs. The adaptor grippers 201 of body adapter 200 embrace a human arm 400 (FIG. 3a) and a human leg 410 (FIGS. 3h and 3c). By using the adapter stripes or grips (201) the adapter is fixed firmly to the patient's body allowing the mechanism to move the endoscope to the desired position.

Figure 4:
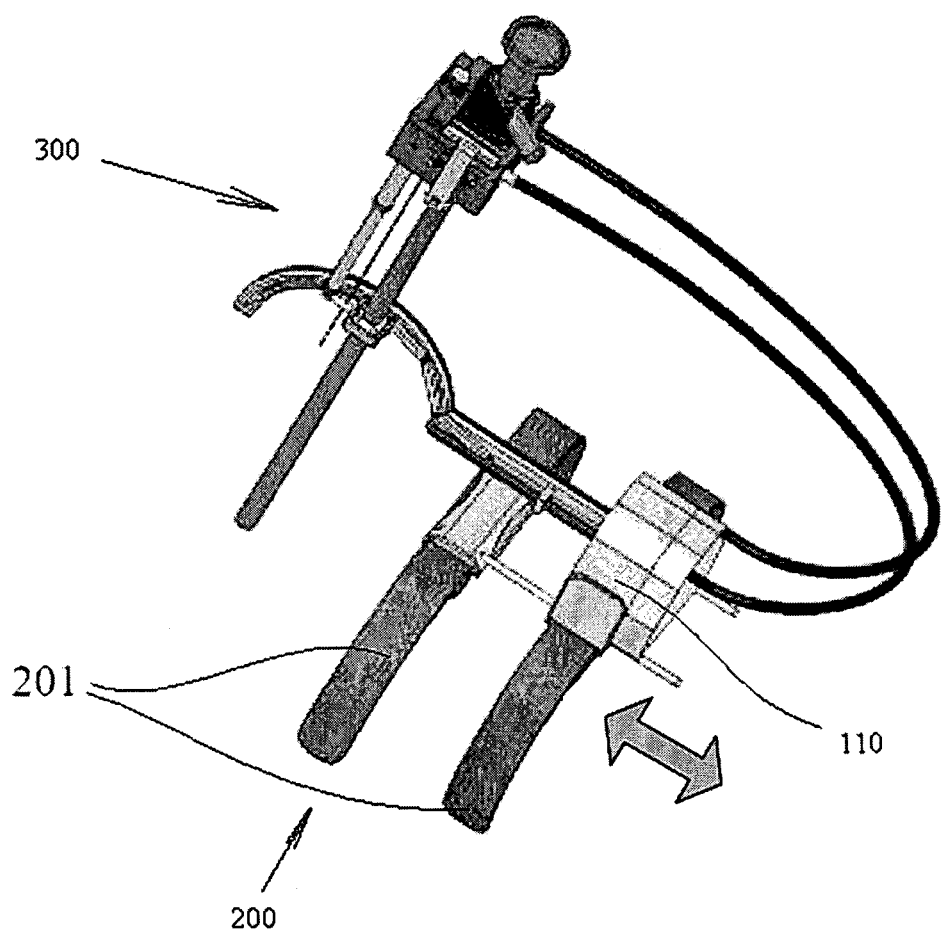
FIG. 4 is a schematic view showing optional displacement provided by a sliding adapter.

Reference is now made to FIG. 4, presenting the motor box 110 which is adapted to move relative to the adapter 200. This option allows the surgeon to attach the first gripper 201 firmly to the patient's limb, and then to position the mechanism 300 in the optimal arrangement relative to a joint incision (not shown) and finally to fix mechanism 300 by the second gripper 201.

Figure 5:
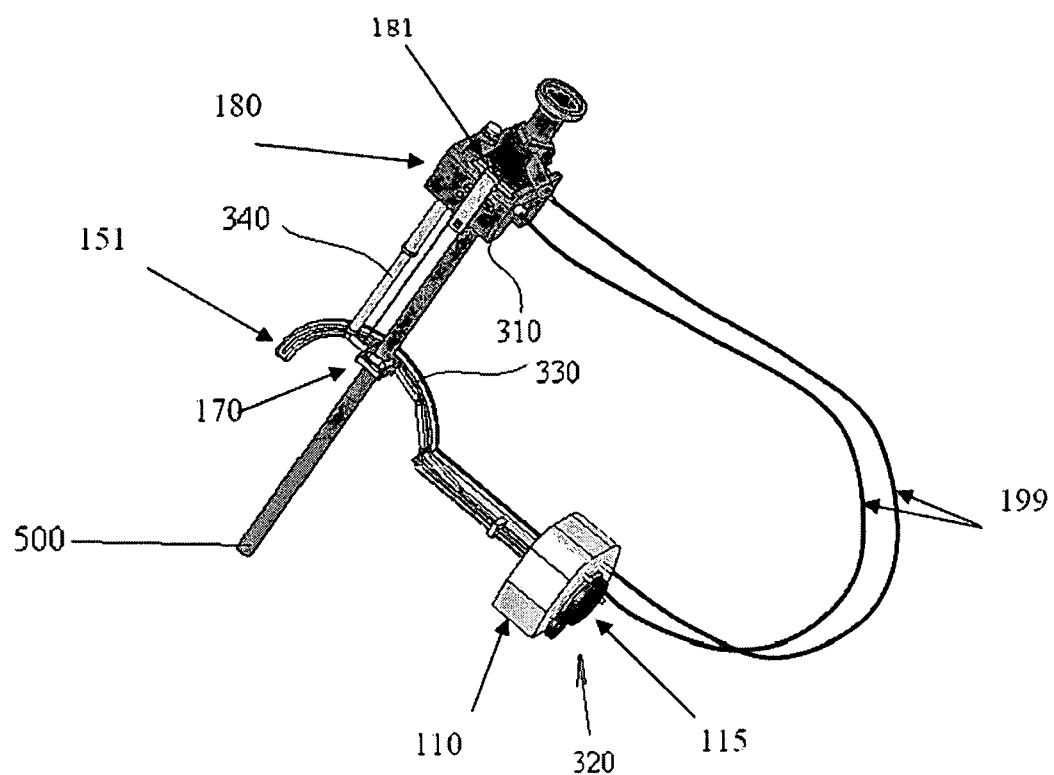
FIG. 5 is a schematic overview of a displacement mechanism.

Reference is now made to FIG. 5, disclosing a motor box 110 that contains the four motors. The transmission 115 transmits motion from the motors located in the motor box 110 to a tilting sub-mechanism 320 and to the arc sub-mechanism 330. Driving the zoom and rotation sub-mechanisms is performed by means of flexible shafts 199. The endoscope 500 passes through a transmission box 180 and a gimbal 170.

Figure 6:
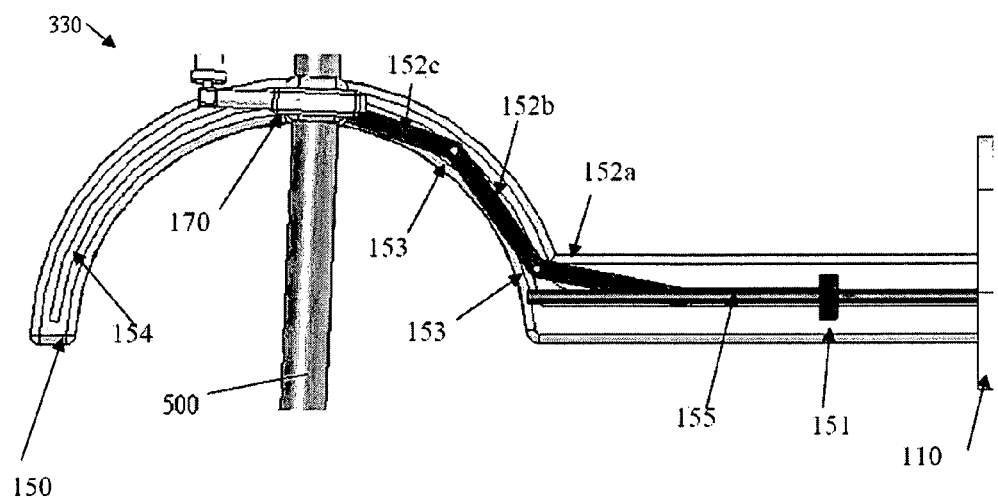
FIG. 6 is a schematic diagram of a sub-mechanism of arc reciprocal displacement.

Reference is now made to FIG. 6 illustrating the arc sub-mechanism 330. A nut 151 is connected to a first link 152a. Hinges 153 are used for coupling links 152b, 152c, etc. Said hinges 153 and links 152a, 152b et cetera are located in semicircular guide 154. The number of the links 152b, 152c, etc., illustrated does not limit the described embodiment. The gimbal 170 is coupled with hinge 153 to the distal end of the last link in the chain. The endoscope 500 passes through the inner part of the gimbal 170. When the screw 155 rotates, the nut moves along the screw, thereby causing the first link 152a in the chain to move in tandem. The other links are forced to move along the semicircular track 154, thus moving the gimbal 170. Due to its being fixed to the gimbal 170, the endoscope 500 moves along the arc 150.

Figure 7:
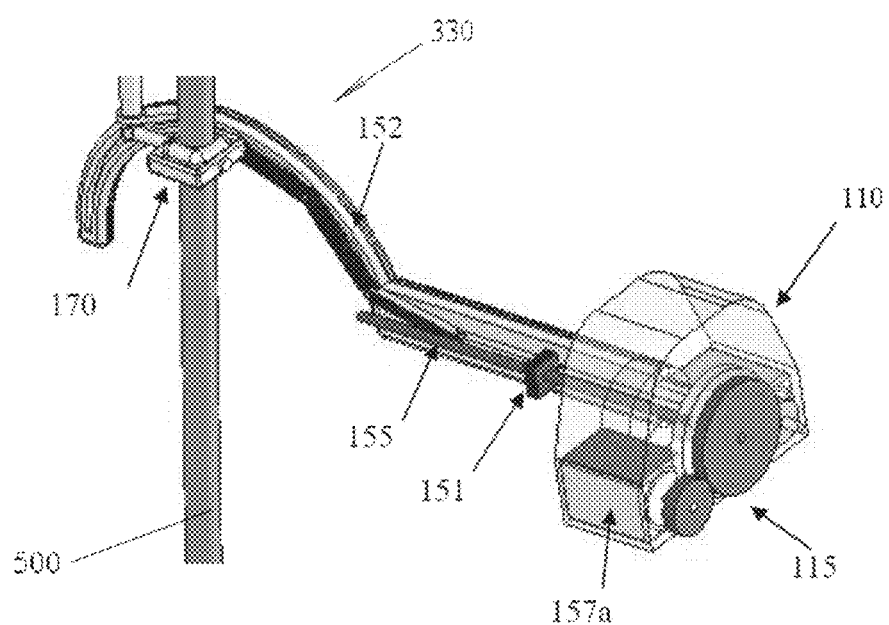
FIG. 7 is a detailed view of a sub-mechanism of arc reciprocal displacement.

Reference is now made to FIG. 7, illustrating the transmission. 115 transmits rotational motion from a motor 157a to the screw 155. The nut 151 moves along the screw 155 and acts upon the link 152a. The nut is connected to a chain of links 152 by means of a fast release mechanism (not shown). The link chain 152 is connected to the gimbal 170 that moves the endoscope 500 along the arc.

Figure 8:
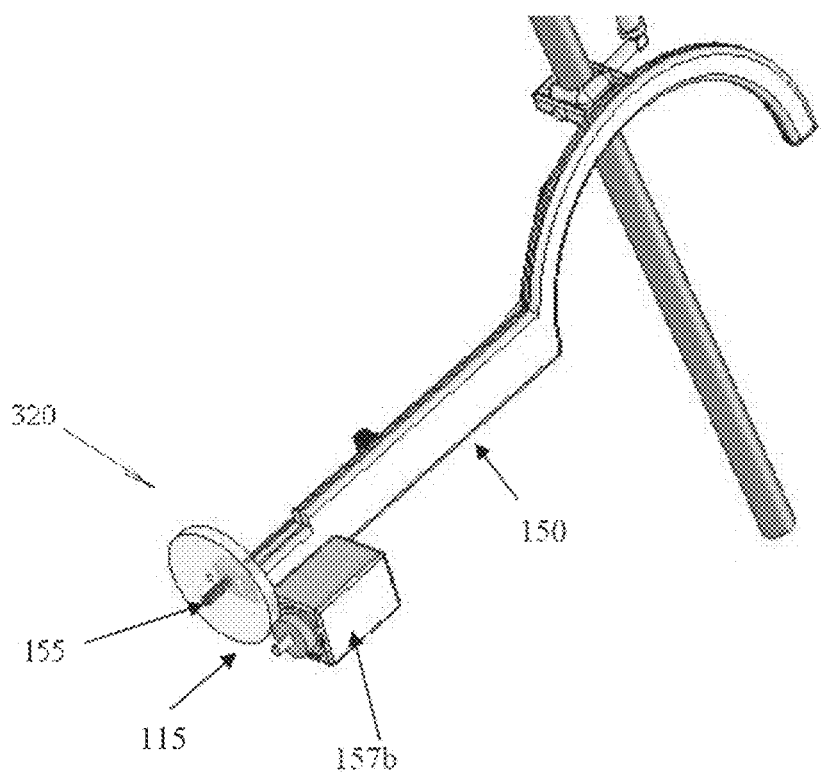
FIG. 8 is a detailed view of a tilting sub-mechanism.

Reference is now made to FIG. 8 showing the main components of the tilting sub-mechanism 320. The transmission 115 transmits rotational motion from a motor 157b to the arc 150 tilting the arc 150 at an angle of interest. Reciprocal movement of the gimbal 170 along the arc 150 and tilting the arc 150 are completely independent.

Figure 9:
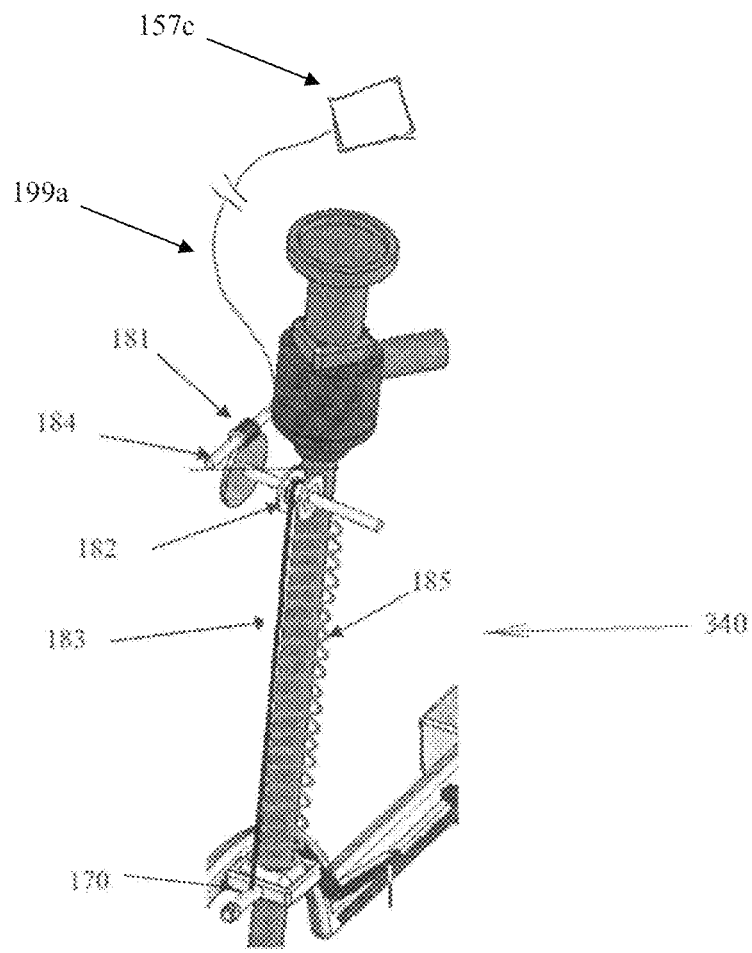
FIG. 9 is a detailed view of a zoom sub-mechanism.

Reference is now made to FIG. 9 presenting the zoom sub-mechanism 340. A flexible shaft 199a couples a motor 157e located in the motor box 110 (not shown) to an axle 184 of a worm gear 181. A drum 182 mechanically connected to the worm gear 181 winds the wire 183 up, so that the distance between the drum 182 and the gimbal 170 becomes shorter. When the motor stops moving, the spring 185 maintains tension in wire 183. The structure of the worm gear prevents the spring 185 from causing undesired displacement of the transmission box 180. During zoom down movement, the motor 157c rotates in the opposite direction. The unwrapped wire 183 lets the spring 183 extend. As a result the zoom box transmission rises.

Figure 10:
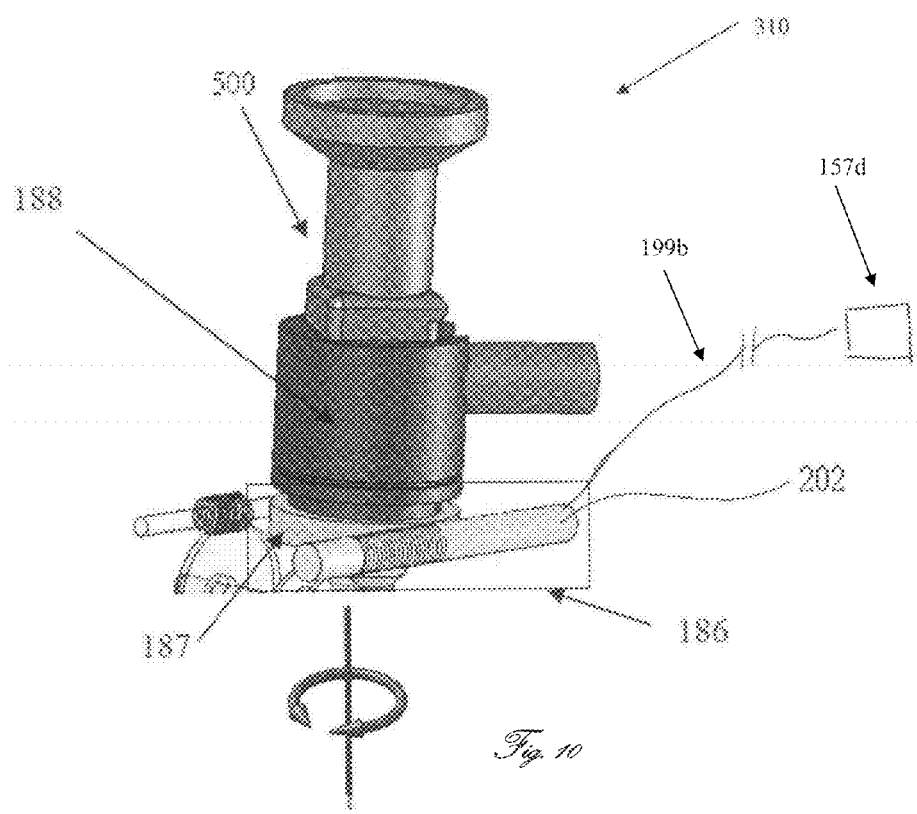
FIG. 10 is a detailed view of a rotation sub-mechanism.

Reference is now made to FIG. 10 showing the rotation sub-mechanism 310. A flexible shaft 199b couples a motor 157d located in motor box 110 (not shown) to an axle 202 of a worm gear 186 which rotates a cogwheel 187. A part of the transmission, the cogwheel 187, allows the endoscope to pass through a hole in its center. The friction between the cogwheel 187 and the endoscope is high enough not to allow circular sliding between them. The aforesaid cog wheel 187 has a centered passage for a proximal portion of the endoscope 500. A locking sub-mechanism (not shown) is adapted to fix and release the endoscope 500.

Another option is to use the housing 188 in order to transmit the rotation from the cogwheel by using the housing to apply the moment on the endoscope head.

Figure 11A:
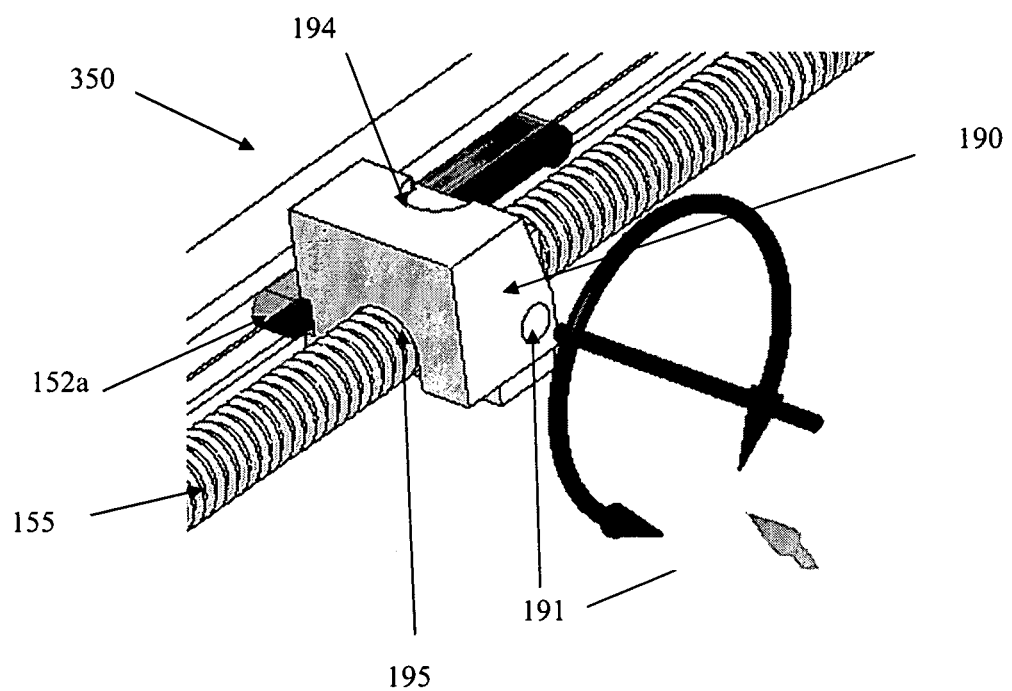
FIG. 11*a* is an isometric view of a locking sub-mechanism.
Figure 11B:
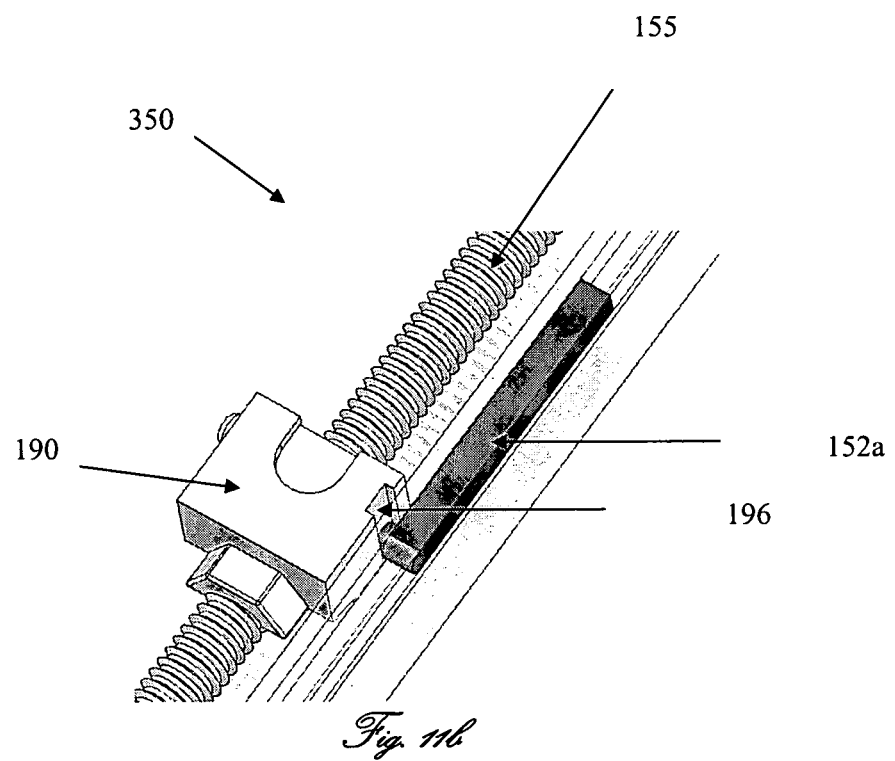
FIG. 11*b* is an isometric view of a locking sub-mechanism in the locked position.
Figure 11O:
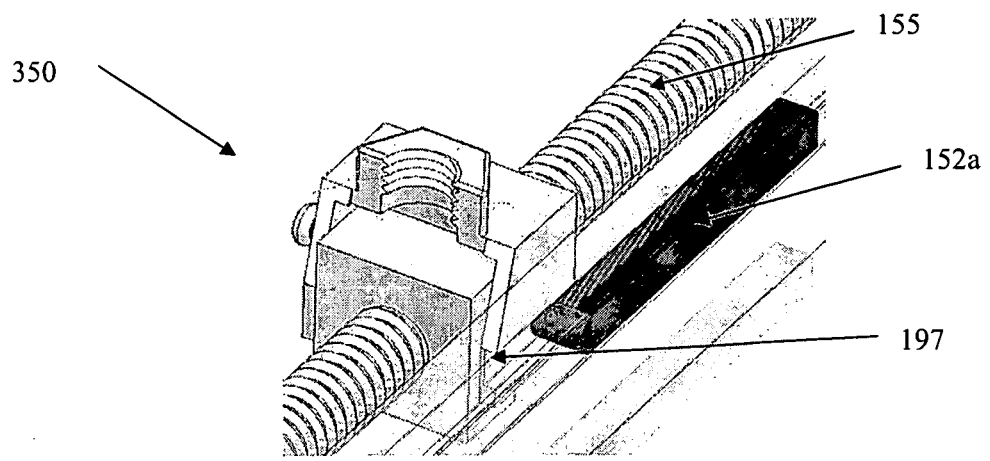
FIG. 11*c* is an isometric view of a locking sub-mechanism in the unlocked position.

Reference is now made to FIGS. 11a, 11b, and 11c, presenting a quick locking sub-mechanism 350 for enabling or disenabling the arcing mechanism 330. The sub-mechanism 350 consists of a lever 190 furnished with two perpendicular slots 196 and 197. The lever 190 can rotate around an axis 191 (FIG. 11a).

In a locked position, the hinge 153 of link 152a is trapped within slot 196 (see FIG. 11b). In an unlocked position the lever is rotated (around axis 191) and enables insertion of link 152a into the slot 197 (see FIG. 11c). An appropriate position of the lever 190 is kept by openings 194 and 195. The openings 194 and 195 are fixed by the screw 155.

Figure 12A:
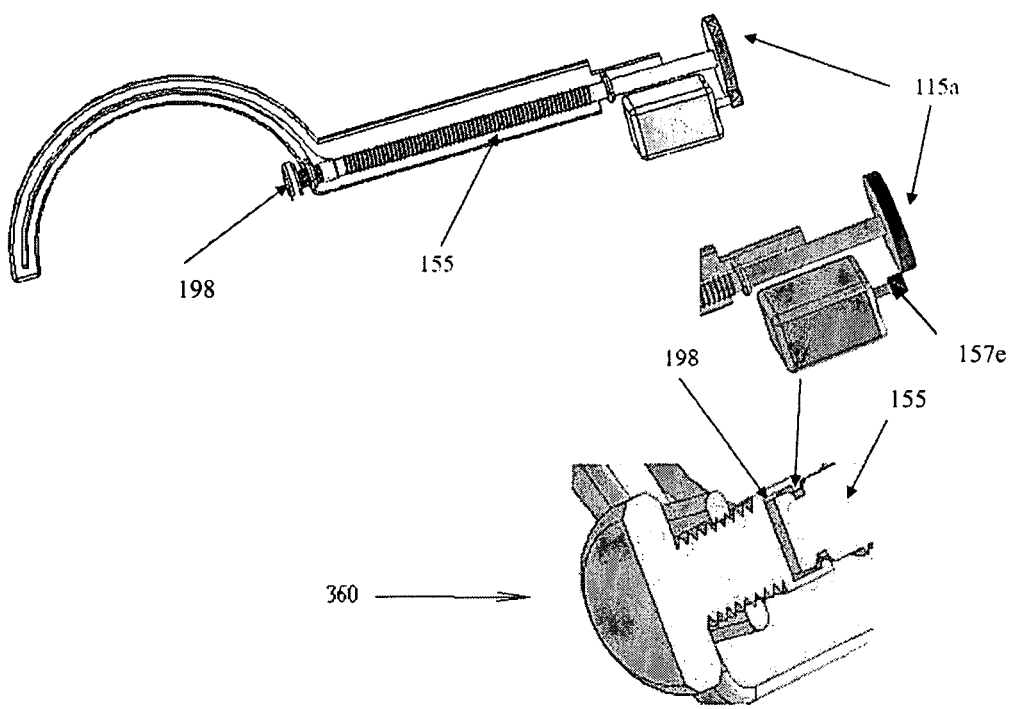
FIG. 12*a* is a detailed view of a coupling/decoupling sub-mechanism.
Figure 12B:
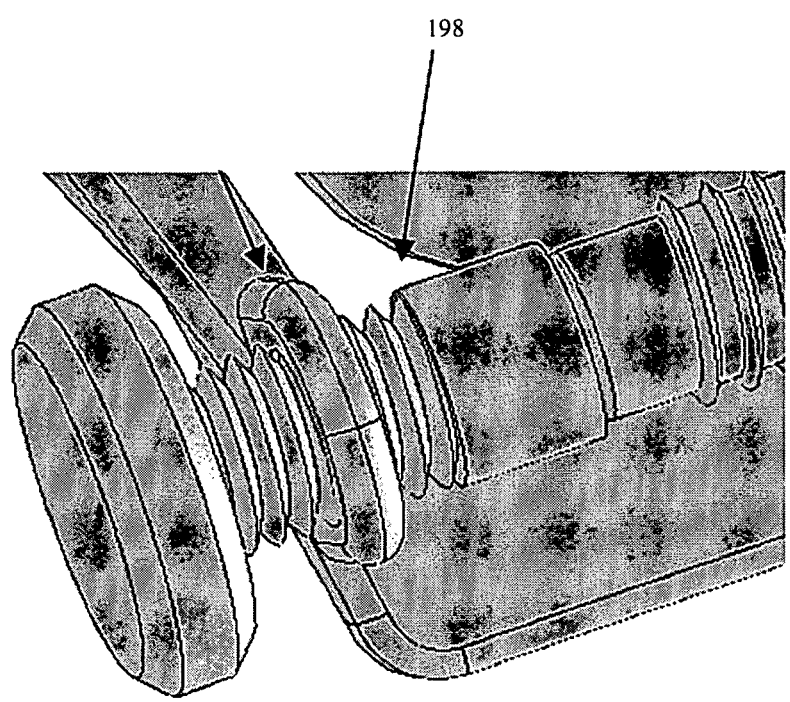
FIG. 12*b* is an enlarged view of a screw of the coupling/decoupling sub-mechanism.

Reference is now made to FIG. 12a and 12b, showing a coupling/decoupling sub-mechanism 360. The sub-mechanism 360 connects and disconnects the arcing mechanism 330 of the endoscope positioning device. The mechanism 360 connects/disconnects the arcing mechanism 330 to/from the motor to which it is connected to enable manual movement of the arcing mechanism 330.

The mechanism 360 consists of a screw 198 that couples/decouples the screw 155 to the transmission 115.

Clockwise rotation of the screw 198 pushes the screw 155 backward, leading to separation of the screw 155 from the transmission 115 and thus disconnection from motor 157e. Conversely, counterclockwise rotation of the screw 198 results in engagement of the screw 155 with transmission 115 and thus engagement with motor 157e. By coupling/decoupling of the transmission 115a to/from motor 157e, the operator can transform to/from a manual mode of operation (or alternatively from/to automatic mode of action).

Figure 13A:
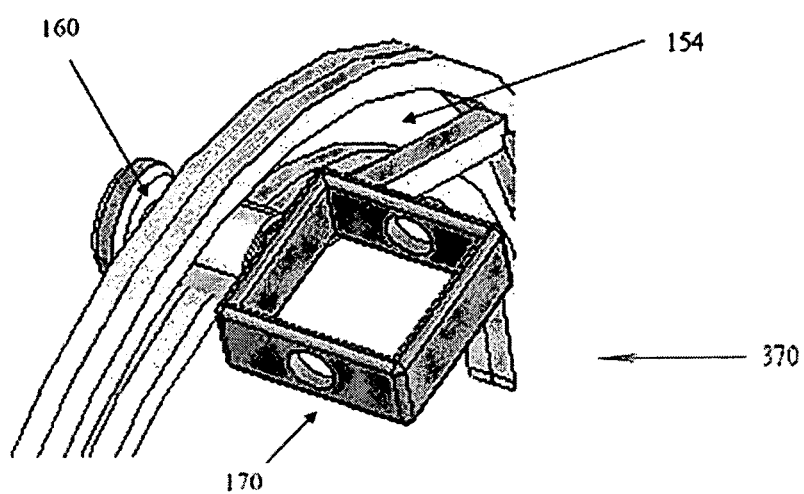
FIG. 13*a* is a schematic view representing an endoscope fixing sub-mechanism on the arc guides; and, FIG. 13*b* is a schematic view representing an endoscope gripping unit alone.
Figure 13B:
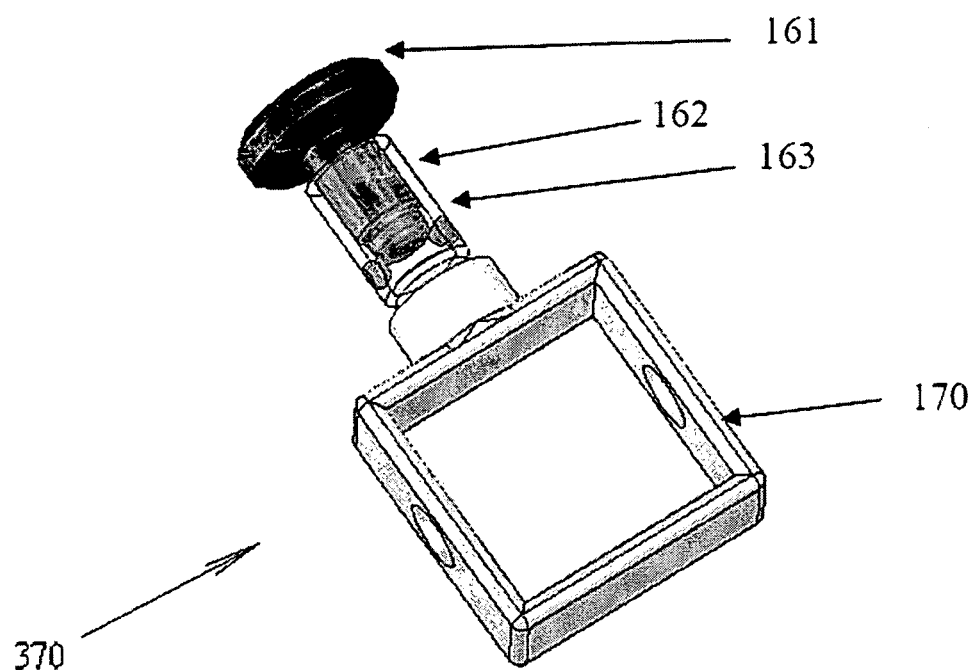

Reference is now made to FIGS. 13a and 13b, disclosing a quick fixing sub-mechanism 370 that enables connection and disconnection of the endoscope 500 and the gimbal 170 to/from arc 151. This feature is of great significance for such operations when the surgeon needs/wants to switch modes or to clean the endoscope 500.

The gimbal 170 is mechanically coupled to a cylinder 162 that serves as a hinge. The cylinder 162 abuts against clamping means (e.g., balls) 163 which apply pressure on the gimbal 170, thus prohibiting its release from cylinder 162.

Disconnection of the gimbal 170 from the cylinder 162 is attained by rotating the screw 161 counterclockwise. The pressure applied by the clamping means (balls 163) on the gimbal is eliminated, such that gimbal 170 and cylinder 162 can be pulled out from screw 161.

When screw 161 is rotated clockwise, balls 163 are pushed out towards cylinder 162 thereby applying pressure on said cylinder. The pressure applied on the cylinder prevents gimbal 170 from disconnecting.

As stated above, the endoscope positioning system 300 is installed on the human limb. Precise positioning provided by the four freedom degree mechanism 100 enables alignment of the position of the endoscope 500 before insertion into a human joint and displacement of a distal end of the endoscope 500 inside the human joint. Rigid fixing of the endoscope 500 relative to the human limb provides freedom for the surgeon's hands from holding or maneuvering the endoscope 500 during a surgical operation.

The invention claimed is:

1. An endoscope positioning system (300) for maneuvering, orienting and positioning an endoscope (500) relative to an organ upon which an operation is being performed, said organ located within a patient's body;
    said endoscope positioning system comprising:
    a. a four freedom degree mechanism (100); said four freedom degree mechanism actuates the distal portion of said endoscope by maneuvering the proximal portion of said endoscope; said four freedom degree mechanism comprises at least a first, second, third and fourth means for providing said four degrees of freedom:
        i. said means of first degree of freedom is a rotation sub-mechanism (310) adapted to rotate said endoscope around the longitudinal axis of said endoscope;
        ii. said means of second degree of freedom is a tilting sub-mechanism (320), comprising:
            a. at least one transmission (115) in mechanical communication with an arc (150); said arc (150) is in mechanical communication with said endoscope; and,
            b. at least one motor (157b) in reversible mechanical communication with said transmission (115);
            said transmission (115) is adapted to transmit rotational motion from said motor (157b) to said arc (150) such that said arc (150) is titled at an angle of interest;
        iii. said means of third degree of freedom is an arc sub-mechanism (330), comprising:
            a. at least one nut (151) adapted to linearly move along at least one screw (155);
            b. a chain comprising a plurality of links, said chain is characterized by having a distal end and a proximal end; each of said links is in mechanical communication with at least one of its neighboring links; said chain is at least partially located in a semicircular guide (154);
            said at least one nut (151) is in mechanical communication with at least one first link (152a) in said proximal end of said chain;
            a gimbal (170) through which said endoscope passes, said gimbal in mechanical communication with at least one link located at said distal end of said chain;
            whereby said linear movement of said nut (151) along said screw causes said first link (152a) in said chain to move along said semicircular guide such that the remaining links in said chain are forced to move along said semicircular guide (154) so as to move said gimbal (170) and said endoscope (500) along said semicircular guide (154);
        iv. said means of fourth degree of freedom is a zoom mechanism (340);
        each of said first, second, third and fourth degrees of freedom is characterized by an independent movement;
    b. at least one body adapter gripper (201) adapted to reversibly and firmly attach said endoscope positioning system to said patient's body;
    wherein said endoscope positioning system conforms to movements of said organ by means of said gripper (201) such that the orientation of said endoscope is adjustable in conjunction with said movements of said organ;
    wherein said zoom mechanism (340) comprises:
    a. at least one worm gear (181);
    b. at least one drum (182) mechanically connected to said worm gear (181); said drum (182) is characterized by a main longitudinal axis; said drum (182) is adapted to rotate a wire (183) around said main axis, such that the distance between said drum (183) and said gimbal (170) is shortened and a zoom motion is obtained.

2. An endoscope positioning system (300) for maneuvering, orienting and positioning an endoscope (500) relative to an organ upon which an operation is being performed, said organ located within a patient's body;
    said endoscope positioning system comprising:
    a. a four freedom degree mechanism (100); said four freedom degree mechanism actuates the distal portion of said endoscope by maneuvering the proximal portion of said endoscope; said four freedom degree mechanism comprises at least a first, second, third and fourth means for providing said four degrees of freedom:

i. said means of first degree of freedom is a rotation sub-mechanism (310) adapted to rotate said endoscope around the longitudinal axis of said endoscope;

ii. said means of second degree of freedom is a tilting sub-mechanism (320), comprising:
  a. at least one transmission (115) in mechanical communication with an arc (150); said arc (150) is in mechanical communication with said endoscope; and,
  b. at least one motor (157b) in reversible mechanical communication with said transmission (115);
  said transmission (115) is adapted to transmit rotational motion from said motor (157b) to said arc (150) such that said arc (150) is titled at an angle of interest;

iii. said means of third degree of freedom is an arc sub-mechanism (330), comprising:
  a. at least one nut (151) adapted to linearly move along at least one screw (155);
  b. a chain comprising a plurality of links, said chain is characterized by having a distal end and a proximal end; each of said links is in mechanical communication with at least one of its neighboring links; said chain is at least partially located in a semicircular guide (154);
  said at least one nut (151) is in mechanical communication with at least one first link (152a) in said proximal end of said chain;
  a gimbal (170) through which said endoscope passes, said gimbal in mechanical communication with at least one link located at said distal end of said chain;
  whereby said linear movement of said nut (151) along said screw causes said first link (152a) in said chain to move along said semicircular guide such that the remaining links in said chain are forced to move along said semicircular guide (154) so as to move said gimbal (170) and said endoscope (500) along said arc semicircular guide (154);

iv. said means of fourth degree of freedom is a zoom mechanism (340);
  each of said first, second, third and fourth degrees of freedom is characterized by an independent movement;

b. at least one body adapter gripper (201) adapted to reversibly and firmly attach said endoscope positioning system to said patient's body;

c. a quick fixing sub-mechanism (370) adapted to reversibly connect said endoscope (500) from semicircular guides (154); said quick fixing sub-mechanism (370) comprising:
  i. the gimbal (170) through which said endoscopes passes through;
  ii. at least one screw (161);
  iii. a cylinder (162) adapted to partially and reversibly accommodate said screw (161);
  iv. at least one clamping means (163) reversibly housed within said cylinder (162); said clamping means (163) being in mechanical communication with said screw (161); said clamping means (163) are adapted to reversibly apply pressure on said cylinder such that said gimbal (170) is reversibly housed within said cylinder (162);
  wherein said endoscope positioning system conforms to movements of said organ by means of said gripper (201) such that the orientation of said endoscope is adjustable in conjunction with said movements of said organ.

3. An endoscope positioning system (300) for maneuvering, orienting and positioning an endoscope (500) relative to an organ upon which an operation is being performed, said organ located within a patient's body;
  said endoscope positioning system comprising:
  a. a four freedom degree mechanism (100); said four freedom degree mechanism actuates the distal portion of said endoscope by maneuvering the proximal portion of said endoscope; said four freedom degree mechanism comprises at least a first, second, third and fourth means for providing said four degrees of freedom:

i. said means of first degree of freedom is a rotation sub-mechanism (310) adapted to rotate said endoscope around the longitudinal axis of said endoscope;

ii. said means of second degree of freedom is a tilting sub-mechanism (320), comprising:
    a. at least one transmission (115) in mechanical communication with an arc (150); said arc (150) is in mechanical communication with said endoscope; and,
    b. at least one motor (157b) in reversible mechanical communication with said transmission (115);
    said transmission (115) is adapted to transmit rotational motion from said motor (157b) to said arc (150) such that said arc (150) is titled at an angle of interest;

iii. said means of third degree of freedom is an arc sub-mechanism (330), comprising:
    a. at least one nut (151) adapted to linearly move along at least one screw (155);
    b. a chain comprising a plurality of links, said chain is characterized by having a distal end and a proximal end; each of said links is in mechanical communication with at least one of its neighboring links; said chain is at least partially located in a semicircular guide (154);
    said at least one nut (151) is in mechanical communication with at least one first link (152a) in said proximal end of said chain;
    a gimbal (170) through which said endoscope passes, said gimbal in mechanical communication with at least one link located at said distal end of said chain;
    whereby said linear movement of said nut (151) along said screw causes said first link (152a) in said chain to move along said semicircular guide such that the remaining links in said chain are forced to move along said semicircular guide (154) so as to move said gimbal (170) and said endoscope (500) along said arc semicircular guide (154);

iv. said means of fourth degree of freedom is a zoom mechanism (340);
    each of said first, second, third and fourth degrees of freedom is characterized by an independent movement;

b. at least one body adapter gripper (201) adapted to reversibly and firmly attach said endoscope positioning system to said patient's body;
  wherein said endoscope positioning system conforms to movements of said organ by means of said gripper (201) such that the orientation of said endoscope is adjustable in conjunction with said movements of said organ;
  wherein said organ is constantly moved during said operation;

further wherein said endoscope positioning system (300) additionally comprising a quick fixing sub-mechanism (370) adapted to reversibly connect said endoscope (500) from semicircular guides (154); said quick fixing sub-mechanism (370) comprising:
  i. the gimbal (170) through which said endoscopes passes through;
  ii. at least one screw (161);
  iii. a cylinder (162) adapted to partially and reversibly accommodate said screw (161);
  iv. at least one clamping means (163) reversibly housed within said cylinder (162); said clamping means (163) being in mechanical communication with said screw (161); said clamping means (163) are adapted to reversibly apply pressure on said cylinder such that said gimbal (170) is reversibly housed within said cylinder (162).

4. The endoscope positioning system according to claim 1, wherein said endoscope positioning system is adapted to maintain a constant orientation of said endoscope relative to said organ by means of said gripper (201), such that alteration in said orientation as a result of said movements of said organ is prevented.

5. The endoscope positioning system according to claim 2, wherein said endoscope positioning system is adapted to maintain a constant orientation of said endoscope relative to said organ by means of said gripper (201), such that alteration in said orientation as a result of said movements of said organ is prevented.

6. The endoscope positioning system according to claim 3, wherein said endoscope positioning system is adapted to maintain a constant orientation of said endoscope relative to said organ by means of said gripper (201), such that alteration in said orientation as a result of said movements of said organ is prevented.

7. The endoscope positioning system according to claim 1, wherein said gripper is selected from the group consisting of strips, magnets, screws, hooks, zips, fasteners, clips, flaps, claspers, springs, grips, hook-and-loop fasteners, hooks, hooks and eyes, straps, strings, wires, cables, tabs, links, poppers, nails, buttons, brackets, buckles and any combination thereof.

8. The endoscope positioning system according to claim 2, wherein said gripper is selected from the group consisting of strips, magnets, screws, hooks, zips, fasteners, clips, flaps, claspers, springs, grips, hook-and-loop fasteners, hooks, hooks and eyes, straps, strings, wires, cables, tabs, links, poppers, nails, buttons, brackets, buckles and any combination thereof.

9. The endoscope positioning system according to claim 3, wherein said gripper is selected from the group consisting of strips, magnets, screws, hooks, zips, fasteners, clips, flaps, claspers, springs, grips, hook-and-loop fasteners, hooks, hooks and eyes, straps, strings, wires, cables, tabs, links, poppers, nails, buttons, brackets, buckles and any combination thereof.

10. The endoscope positioning system according to claim 1, wherein said tilting sub-mechanism (320) is characterized in that the reciprocal movement of said gimbal (170) along arc (150), and tilting of arc (150) are completely independent movements.

11. The endoscope positioning system according to claim 2, wherein said tilting sub-mechanism (320) is characterized in that the reciprocal movement of said gimbal (170) along arc (150), and tilting of arc (150) are completely independent movements.

12. The endoscope positioning system according to claim 3, wherein said tilting sub-mechanism (320) is characterized in that the reciprocal movement of said gimbal (170) along arc (150), and tilting of arc (150) are completely independent movements.

13. The endoscope positioning system according to claim 2, wherein said zoom mechanism (340) comprises:
  a. at least one worm gear (181);
  b. at least one drum (182) mechanically connected to said worm gear (181); said drum (182) is characterized by a main longitudinal axis; said drum (182) is adapted to rotate a wire (183) around said main axis, such that the distance between said drum (183) and said gimbal (170) is shortened and a zoom motion is obtained.

14. The endoscope positioning system according to claim 3, wherein said zoom mechanism (340) comprises:
  a. at least one worm gear (181);
  b. at least one drum (182) mechanically connected to said worm gear (181); said drum (182) is characterized by a main longitudinal axis; said drum (182) is adapted to rotate a wire (183) around said main axis, such that the distance between said drum (183) and said gimbal (170) is shortened and a zoom motion is obtained.

15. The endoscope positioning system according to claim 2, additionally comprising a quick locking sub-mechanism (350), adapted to enable or disenable said arc sub-mechanism (330).

16. The endoscope positioning system according to claim 3, additionally comprising a quick locking sub-mechanism (350), adapted to enable or disenable said arc sub-mechanism (330).

17. The endoscope positioning system according to claim 1, wherein said operation is an orthopedic operation.

18. The endoscope positioning system according to claim 17, wherein said organ is moved continuously throughout said operation.

19. The endoscope positioning system according to claim 2, wherein said operation is an orthopedic operation.

20. The endoscope positioning system according to claim 19, wherein said organ is moved continuously throughout said operation.

21. The endoscope positioning system according to claim 1, additionally comprising a quick locking sub-mechanism (350), adapted to enable or disenable said arc sub-mechanism (330).

\* \* \* \* \*